United States Patent
Pochorovski et al.

(10) Patent No.: US 10,793,667 B2
(45) Date of Patent: Oct. 6, 2020

(54) CURABLE COMPOSITIONS, PRODUCTS AND ARTICLES FORMED THEREFROM, AND METHODS OF FORMING THE SAME

(71) Applicants: Covestro Deutschland AG, Leverkusen (DE); COVESTRO LLC, Pittsburgh, PA (US)

(72) Inventors: Igor Pochorovski, Bergisch Gladbach (DE); Alan Ekin, Coraopolis, PA (US)

(73) Assignees: Covestro Deutschland AG, Leverkusen (DE); Covestro LLC, Pittsburgh, PA (US)

( * ) Notice: Subject to any disclaimer, the term of this patent is extended or adjusted under 35 U.S.C. 154(b) by 49 days.

(21) Appl. No.: 16/269,600

(22) Filed: Feb. 7, 2019

(65) Prior Publication Data
US 2020/0255585 A1   Aug. 13, 2020

(51) Int. Cl.
| | |
|---|---|
| C08G 18/83 | (2006.01) |
| C08J 3/24 | (2006.01) |
| C09D 175/04 | (2006.01) |
| C09K 3/10 | (2006.01) |
| C09J 175/04 | (2006.01) |
| C08G 18/28 | (2006.01) |
| C08G 101/00 | (2006.01) |

(52) U.S. Cl.
CPC ....... *C08G 18/833* (2013.01); *C08G 18/2875* (2013.01); *C08J 3/24* (2013.01); *C09D 175/04* (2013.01); *C09J 175/04* (2013.01); *C09K 3/1021* (2013.01); *C08G 2101/00* (2013.01); *C09K 2200/065* (2013.01)

(58) Field of Classification Search
None
See application file for complete search history.

(56) References Cited

U.S. PATENT DOCUMENTS

| | | |
|---|---|---|
| 4,118,422 A | 10/1978 | Klein |
| 5,663,262 A | 9/1997 | Shirakawa et al. |
| 7,183,360 B2 | 2/2007 | Daniel et al. |
| 2004/0003996 A1 | 1/2004 | Anderson et al. |
| 2005/0187314 A1* | 8/2005 | Anderson ............ C08G 18/807 523/415 |

FOREIGN PATENT DOCUMENTS

| | | |
|---|---|---|
| CN | 105315470 A | 2/2016 |
| WO | 2016077147 A1 | 5/2016 |

OTHER PUBLICATIONS

Kupryushkin et al., Efficient Functionalization of Oligonucleotides by New Achiral Nonnucleosidic Monomers, Organic Letters, American Chemical Society, 2014, vol. 16, pp. 2842-2845.

Maxim S. Kupryushkin, Dmitrii A. Konevetz, Svetlana V. Vasilyeva, Anastasia S. Kuznetsova, Dmitry A. Stetsenko & Dmitrii V. Pyshnyi (2013) Oligonucleotide Functionalization by a Novel Alkyne-Modified Nonnucleosidic Reagent Obtained by Versatile Building Block Chemistry, Nucleosides, Nucleotides and Nucleic Acids, 32:6, pp. 306-319.

* cited by examiner

*Primary Examiner* — Christopher M Rodd
(74) *Attorney, Agent, or Firm* — John E. Mrozinski, Jr.

(57) ABSTRACT

A curable composition, a method of making the curable composition, and an article and product produced therefrom are provided. A morpholinedione is contacted with an isocyanate to form a resin composition. The resin composition is reacted with an amine to form the curable composition.

29 Claims, No Drawings

CURABLE COMPOSITIONS, PRODUCTS AND ARTICLES FORMED THEREFROM, AND METHODS OF FORMING THE SAME

FIELD OF THE INVENTION

The present disclosure relates to a curable composition, a method of making the curable composition, and an article produced therefrom.

BACKGROUND OF THE INVENTION

Two-component polyurethane forming compositions are widely used because of the many advantageous properties they exhibit. These compositions generally comprise a liquid binder component and a liquid hardener/crosslinker component. The liquid binder component may comprise an isocyanate-reactive component, such as a polyol, and the liquid crosslinker component may comprise a polyisocyanate. The addition reaction of the polyisocyanate with the isocyanate-reactive component, which can occur at ambient conditions, can produce crosslinked polyurethane networks that form coatings.

SUMMARY OF THE INVENTION

The present disclosure provides a method for forming a curable composition. The method comprises contacting a morpholinedione with an isocyanate to form a resin composition. The resin composition is reacted with an amine to form the curable composition.

The present disclosure also provides an article produced by contacting a morpholinedione with an isocyanate to form a resin composition. The resin composition is reacted with an amine to form the curable composition.

The present disclosure also provides a curable composition. The curable composition comprises the following structure:

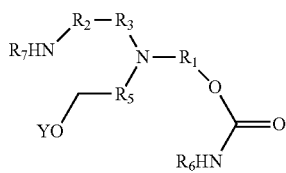

wherein $R_1$ is an alkyl bridging group; two of $R_2$, $R_3$, and $R_5$ are a carbonyl group and the remaining one of $R_2$, $R_3$, and $R_5$ is a methylene bridge; $R_6$ is an alkyl group or an aryl group; $R_7$ is an alkyl group or an aryl group; and Y is at least one of a hydrogen atom, an alkyl group, an aryl group, and a carbamate group.

It is understood that the invention disclosed and described in this specification is not limited to the embodiments summarized in this Summary. The reader will appreciate the foregoing details, as well as others, upon considering the following detailed description of various non-limiting and non-exhaustive embodiments according to this specification.

DETAILED DESCRIPTION OF THE INVENTION

Various embodiments are described and illustrated herein to provide an overall understanding of the structure, function, operation, manufacture, and use of the disclosed products and processes. The various embodiments described and illustrated herein are non-limiting and non-exhaustive. Thus, the invention is not limited by the description of the various non-limiting and non-exhaustive embodiments disclosed herein. Rather, the invention is defined solely by the claims. The features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Furthermore, Applicant reserves the right to amend the claims to affirmatively disclaim features or characteristics that may be present in the prior art. The various embodiments disclosed and described in this specification can comprise, consist of, or consist essentially of the features and characteristics as variously described herein.

Any patent, publication, or other disclosure material identified herein is incorporated herein by reference in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference herein.

Reference herein to "certain examples," "some examples," "various non-limiting examples," or the like, means that a particular feature or characteristic may be included in an example. Thus, use of such phrases, and similar phrases, herein does not necessarily refer to a common example, and may refer to different examples. Furthermore, the particular features or characteristics may be combined in any suitable manner in one or more examples. Thus, the particular features or characteristics illustrated or described in connection with various examples may be combined, in whole or in part, with the features or characteristics of one or more other examples. Such modifications and variations are intended to be included within the scope of the present specification. In this manner, the various examples described in this specification are non-limiting and non-exhaustive.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The grammatical articles "a," "an," and "the," as used herein, are intended to include "at least one" or "one or more," unless otherwise indicated, even if "at least one" or "one or more" is expressly used in certain instances. Thus, the articles are used herein to refer to one or more than one (i.e., to "at least one") of the grammatical objects of the article. Furthermore, the use of a singular noun includes the plural, and the use of a plural noun includes the singular, unless the context of the usage requires otherwise.

As used herein, "polymer" encompasses prepolymers, oligomers, and both homopolymers and copolymers; the prefix "poly" in this context referring to two or more.

As used herein, the term "aliphatic" refers to organic compounds characterized by substituted or un-substituted straight, branched, and/or cyclic chain arrangements of constituent carbon atoms. Aliphatic compounds do not contain aromatic rings as part of the molecular structure thereof.

As used herein, the term "cycloaliphatic" refers to organic compounds characterized by arrangement of carbon atoms in closed ring structures. Cycloaliphatic compounds do not contain aromatic rings as part of the molecular structure thereof. Therefore, cycloaliphatic compounds are a subset of aliphatic compounds. Therefore, the term "aliphatic" encompasses aliphatic compounds and/or cycloaliphatic compounds.

As used herein, "isocyanate" refers to a compound containing an isocyanate group. The isocyanate can comprise at least one of a monoisocyanate and a polyisocyanate. As used herein, "diisocyanate" refers to a compound containing two isocyanate groups. As used herein, "polyisocyanate" refers to a compound containing two or more isocyanate groups. Hence, diisocyanates are a subset of polyisocyanates.

As used in this specification, the terms "cure" and "curing" refer to a chemical crosslinking of components in a curable composition and/or a chain extension of the curable composition. Accordingly, the terms "cure" and "curing" do not encompass solely physical drying of curable compositions through solvent or carrier evaporation. In this regard, the term "cured," as used in this specification, refers to the condition of a curable composition in which a component of the curable composition has chemically reacted to form a new covalent bond.

Having a free isocyanate group may be undesirable. Thus, a curable composition, a method of making the curable composition, and an article produced therefrom are provided and they can minimize and/or can eliminate free isocyanate groups and/or a reaction of isocyanate groups during curing of the curable composition. More specifically, a morpholinedione can be contacted with an isocyanate to form a resin composition. The resin composition can be reacted with an amine to form a curable composition.

A morpholinedione comprises a ring structure comprising an amine group, an ether group, and two carbonyl groups. The morpholinedione can comprise a hydroxyl group and, in those examples, the hydroxyl group can be pendant from the amine group in the ring structure. The ring structure can comprise six members and at least one carbonyl group may be adjacent to the ether group such that the adjacent carbonyl group and the ether group form an ester. At least one carbonyl group may be adjacent to the amine group such that the adjacent carbonyl group and the amine group form an amide. The morpholinedione can comprise the Formula I and/or isomers thereof.

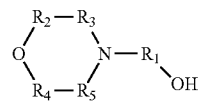

Formula I $R_1$ can be an alkyl bridging group. As used herein, an "alkyl bridging group" means a methylene bridging group (e.g., —$CH_2$—) or a chain of single bonded carbons (e.g., —$CH_2$—$CH_2$—, —$CH_2$—$CH_2$—$CH_2$—). $R_1$ may not present in formula I and the hydroxyl group can be directly attached to the amine group. Two of $R_2$, $R_3$, $R_4$, and $R_5$ can be a carbonyl group and the remaining two of $R_2$, $R_3$, $R_4$, and $R_5$ can be methylene bridges (e.g., —$CH_2$—). As used herein, an "alkyl group" can comprise at least one of an alkyl such as, for example, a methyl (e.g., —$CH_3$), an ethyl (e.g., —$CH_2$—$CH_3$), or a propyl group (e.g., —$CH_2$—$CH_2$—$CH_3$), and an alkyl bridging group. For example, the morpholinedione can comprise N-hydroxyethylmorpholine-2, 3-dione, which comprises Formula II and/or isomers thereof.

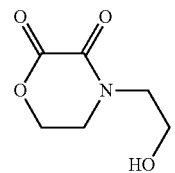

Formula II

The morpholinedione can comprise a reaction product of diethanolamine and a diethyloxalate. For example, the reaction of diethanolamine and a diethyloxalate to form N-hydroxyethylmorpholine-2, 3-dione is illustrated in Scheme I.

Scheme 1

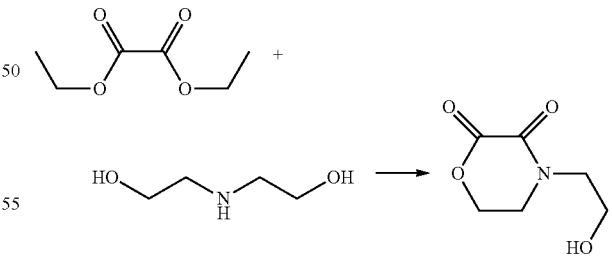

The morpholinedione can be contacted with a first isocyanate to form a resin composition. The first isocyanate can react with the hydroxyl group in the morpholinedione to form an adduct comprising a carbamate (e.g., urethane). The resin composition may include minimal, if any, free isocyanate groups. For example, the resin composition may not include any free isocyanate groups. The resin composition may comprise 2-(morpholine-2, 3-dione)alkyl alkylcarbamate and/or 2-(2, 3-morpohlinedione)alkyl arylcarbamate.

The reaction of the morpholinedione and the first isocyanate to form the resin composition is illustrated in Scheme II.

Scheme II

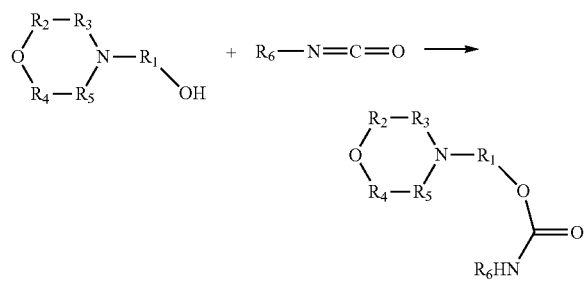

wherein $R_6$ is an alkyl group or an aryl group.

An isocyanate can comprise a mono-isocyanate or a polyisocyanate. When comprising a polyisocyanate, the adduct may include two or more morpholinediones per polyisocyanate. For example, if the polyisocyanate is a diisocyanate, the adduct can comprise two morpholinediones per polyisocyanate.

The polyisocyanate can comprise at least one of an aromatic polyisocyanate, an araliphatic polyisocyanate, and an aliphatic polyisocyanate. The isocyanate can comprise at least one of a polyurethane resin, a polyurea resin, an acrylic resin, a polyester resin, a polycarbonate resin, a polysiloxane resin, an epoxy resin, a melamine resin, and a phenol formaldehyde resin. For example, the isocyanate can comprise at least one of 1,4-tetramethylene diisocyanate, 1,6-hexamethylene diisocyanate, 2,2,4 and 2,4,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate bio-based), 2-methylpentamethylene 1,5-diisocyanate, lysine and lysine ester diisocyanate, 1,4-diisocyanato-2,2,6-trimethylcyclohexane (TMCDI), 1,3- and 1,4-bis(isocyanatomethyl)cyclohexane), m- and p-tetramethyl-1,3-xylylene diisocyanate, m- and p-tetramethyl-1,4-xylylene diisocyanate, bis(1-isocyanato-1-methylethyl)naphthalene, 1,3- and 1,4-phenylene diisocyanate, 2,3,5,6-tetramethyl-1,4-diisocyanatobenzene, naphthalene 1,5-diisocyanate (NID), 3,3'-dimethyl-4,4'-diisocyanatobiphenyl (TOBI); oligomers, polymers, mixtures, and isomers thereof.

The isocyanate can comprise a diisocyanate of the formula $R_x(NCO)_2$, wherein $R_x$ represents an aliphatic hydrocarbon residue having 4 to 12 carbon atoms, a cycloaliphatic hydrocarbon residue having 6 to 15 carbon atoms, an aromatic hydrocarbon residue having 6 to 15 carbon atoms or an araliphatic hydrocarbon residue having 7 to 15 carbon atoms. The isocyanate can have an isocyanate calculated functionality of two or more such as, for example, three or more (calculated from isocyanate content and number average molecular weight, determined by Gel Permeation Chromatography (GPC) measurement).

The isocyanate can comprise at least one of a polyisocyanate comprising a biuret group, such as the biuret adduct of hexamethylene diisocyanate (HDI) available from Covestro AG under the trade designation DESMODUR N-100, a polyisocyanate containing an isocyanurate group, such as that available from Covestro AG under trade designation DESMODUR N-3300, a polyisocyanate such as that available from Covestro AG under the tradename DESMODUR N-3600, which has a viscosity of 800-1400 mPa·s at 25° C., and a polyisocyanate containing at least one of an iminooxadiazine dione group, a urethane group, a uretdione group, a carbodiimide group, and an allophanate group.

In forming the resin composition according to the present disclosure, the isocyanate and morpholinedione may be combined in relative amounts such that the resin composition has a ratio of isocyanate groups to isocyanate-reactive groups (e.g., hydroxyl group) in an effective ratio for a curing process. For example, the resin composition may have a ratio of isocyanate groups to isocyanate-reactive groups (e.g., hydroxyl group) of 0.01:1 to 3.0:1, such as, for example, 0.8:1 to 3.0:1, 0.5:1 to 2.0:1, 0.8:1 to 2.0:1, 0.8:1 to 1.2:1, 0.9:1 to 1:1, 0.9:1 to 1.1:1, 1:1 to 1.1:1, 1:1 to 1.8:1, or 1:1 to 1.5:1. The resin composition may have a ratio of isocyanate groups to isocyanate-reactive groups (e.g., hydroxyl group) of at least 0.01:1, such as, for example, at least 0.5:1, at least 0.8:1, at least 0.9:1, at least 1:1, at least 1.1:1, at least 1.2:1, at least 1.5:1, or at least 2.0:1. The resin composition may have a ratio of isocyanate groups to isocyanate-reactive groups (e.g., hydroxyl group) of no greater than 3.0:1, such as, for example, no greater than 2.0:1, no greater than 1.5:1, no greater than 1.2:1, no greater than 1.1:1, no greater than 1.1:1, no greater than 0.9:1, no greater than 0.8:1, or no greater than 0.5:1.

The resin composition can comprise a catalyst for the reaction between the isocyanate-reactive group and the isocyanate group. The catalyst can comprise at least one of a metallic catalyst and/or a nonmetallic catalyst, such as, for example, an amine catalyst (e.g., 1,8-diazabicyclo[5.4.0]undec-7-ene (DBU), 1,4-diazabicyclo[2.2.2]octane (DABCO) or triethanolamine), a Lewis acid compound (e.g., dibutyltin dilaurate), lead octoate, tin octoate, a titanium complex, a zirconium complex, a cadmium compound, a bismuth compound (e.g., bismuth neodecanoate), and an iron compound. The catalyst can be present in the resin composition in an amount of no more than 3.0% by weight based on the total solids contents of the composition.

Where the morpholinedione comprises N-hydroxyethyl-morpholine-2, 3-dione, the morpholinedione can react with the first isocyanate to form a resin composition comprising 2-(morpholine-2, 3-dione)ethyl akylcarbamate and/or 2-(2, 3-morpholinedione)ethyl arylcarbamate as illustrated in Scheme III.

Scheme III

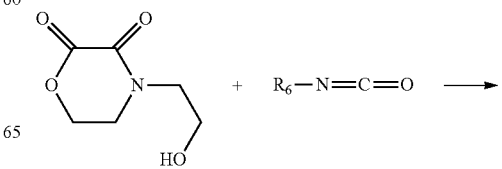

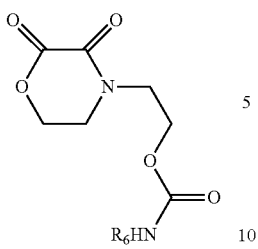

The resin composition can be reacted with an amine to form the curable composition. The curable composition can be an adduct of the amine and the resin composition. The reaction may include minimal, if any, free isocyanate groups. For example, the present disclosure provides the reaction in which the resin composition with the amine may not include the reaction of a free isocyanate group. The reaction of the resin composition and the amine can comprise a ring opening reaction. For example, the amine can react with the ester group in the morpholinedione to dissolve the bond between the oxygens in the ester group and, thus, open the ring of the cycloaliphatic compound in the resin composition. The reaction of the resin composition and the amine can comprise a cross-linking of the resin composition with the amine (e.g., 0.01-100% crosslinked). For example, the reaction of the resin composition and the amine to form the curable composition is illustrated in Scheme IV.

Scheme IV

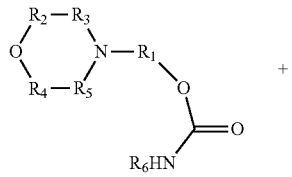

+ R_7NH_2 ⟶

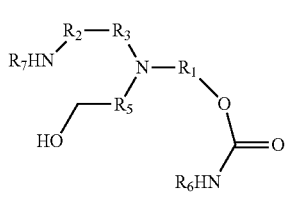

wherein $R_7$ is an alkyl group or an aryl group.

The amine may be a primary amine. The amine may comprise at least one of diethylenetriamine, 2-methylpentamethylenediamine, isophrone diamine, 4,4'-diaminodicyclohexylmethane, 3, 3'-dimethyl-4, 4'diaminodicyclohexylmethane, ethylene diamine, ethylene triamine, propylene diamine, tetramethylene diamine, 1,6-hexamethylene diamine, bis(6-aminohexyl)ether, tricyclodecane diamine, N,N'-dimethyldiethyltriamine, cyclohexyl-1,2,4-triamine, cyclohexyl-1,2,4,5-tetraamine, 3,4,5-triaminopyran, 3,4-diaminofuran, cycloaliphatic diamines, triaminononane, polyether amine, and a polyaspartic ester based amine.

Where the resin composition was formed from morpholinedione comprising N-hydroxyethylmorpholine-2, 3-dione, the resin composition can react with an amine to form the curable composition as illustrated in Scheme V.

Scheme V

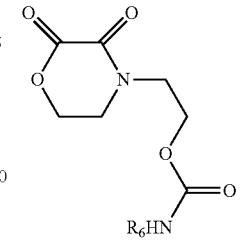 + R_7NH_2 ⟶

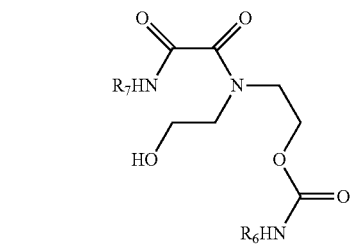

The curable composition can be reacted with an additional reactant (X) to form a secondary composition. The additional reactant can react with the free hydroxyl group in the curable composition to form the secondary composition as illustrated in Scheme VI.

Scheme VI

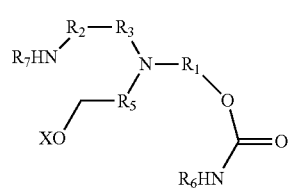

The additional reactant can be various chemicals suitable to react with the free hydroxyl group in the curable composition. The additional reactant may be, for example, at least one of a second isocyanate, a silane, and a melamine. The second isocyanate may be different than or the same as the first isocyanate. In examples where the first and second isocyanates are different, the curable composition can comprise unique properties otherwise unattainable with only the first isocyanate or only the second isocyanate.

Where the curable composition was formed from morpholinedione comprising N-hydroxyethylmorpholine-2, 3-dione, the reaction of the curable composition with a second isocyanate to form the secondary composition is illustrated in scheme VII.

Scheme VII

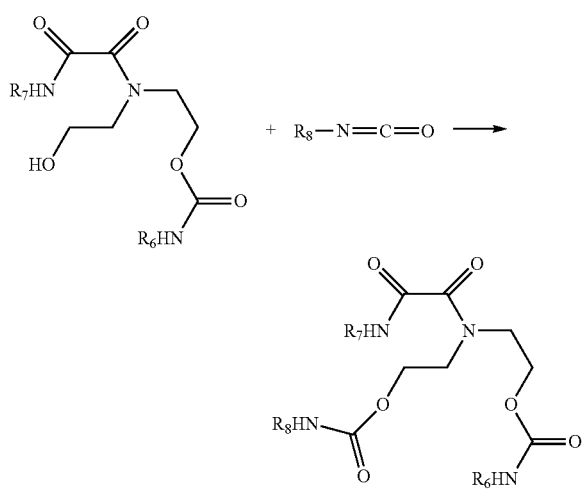

wherein $R_8$ is an alkyl group or an aryl group. $R_6$ and $R_8$ can be the same alkyl group or aryl group or can comprise the same alkyl group or aryl group. $R_6$ and $R_8$ can comprise at least one of an aliphatic hydrocarbon residue having 4 to 12 carbon atoms, a cycloaliphatic hydrocarbon residue having 6 to 15 carbon atoms, an aromatic hydrocarbon residue having 6 to 15 carbon atoms or an araliphatic hydrocarbon residue having 7 to 15 carbon atoms. For example, $R_6$ and $R_8$ both can comprise butane. $R_6$ can comprise butane while $R_8$ can comprise hexane. $R_6$ can comprise hexane while $R_8$ can comprise cyclopentane. The method according to the present disclosure can enable the addition of different chemical groups to the secondary composition through the use of at least two different reaction steps with two different isocyanates.

Schemes II-VII illustrate a subunit of a polymer through different stages of a polymerization reaction and should not be considered limiting of a length, configuration, composition, crosslinking, and/or molecular weight of a polymer that can be formed. The isocyanate and amine depicted in Schemes II-VII can have various amounts of active groups as describe herein. Thus, the present disclosure should not be read to limit the isocyanate and resulting structures shown in Schemes II-VII to a monoisocyanate and a polyisocyanate, as described herein, may also be employed. The present disclosure should not be read to limit the amine and resulting structures shown in Schemes IV-VII to a monoamine, as a polyamine, as described herein, may also be employed.

The curable composition and/or secondary composition can be cured to form an article. The curable composition and/or secondary composition can be cured at a temperature in a range of 0° C. to 200° C., such as, for example, 20° C. to 150° C., 25° C. to 140° C., or 80° C. to 140° C. The curable composition and/or secondary composition can be cured at a temperature of at least 20° C., such as, for example, at least 25° C., at least 50° C., at least 80° C., at least 100° C., at least 140° C., or at least 150° C. The curable composition and/or secondary can be cured for at least one minute, such as, for example, at least one hour, at least two hours, at least three hours, at least five hours, at least 10 hours, at least 15 hours, at least 16 hours, or at least 24 hours.

The article can be, for example, a component of at least one of an adhesive, a coating, a casting, a sealant, an elastomer, and a foam.

The cured curable composition and/or cured secondary composition can have a microhardness of at least 2 N/mm², such as, for example, at least 4 N/mm², at least 8 N/mm², at least 10 N/mm², at least 20 N/mm², at least 25 N/mm², at least 50 N/mm², at least 100 N/mm², at least 125 N/mm², or at least 140 N/mm². The microhardness can be measured according to DIN EN ISO 14577-1:2015.

The cured curable composition and/or cured secondary composition can have a methyl ethyl ketone rub resistance of at least 100 double rubs, such as, for example, at least 150 double rubs, at least 180 double rubs, at least 200 double rubs, at least 250 double rubs, or at least 300 double rubs. The methyl ethyl ketone rub resistance can be measured according to ASTM D4752-10(2015).

The cured curable composition and/or cured secondary composition can have a cross-hatch adhesion of at least 4B. For example, the cured curable composition and/or cured secondary composition can have a cross-hatch adhesion of 5B. The cross hatch-adhesion can be measured according to ASTM D 3359-17.

The cured curable composition and/or cured secondary composition can have a direct and reverse impact strength of at least 100 in-lbs, such as, for example, at least 150 in-lbs. Direct and reverse impact strength can be measured according to ASTM D 2794-93(2019).

The cured curable composition and/or cured secondary composition can have a water spot resistance of at least one hour, such as, for example, at least two hours, at least four hours, at least 10 hours, at least 16 hours, at least 20 hours, or at least 24 hours. Water spot testing can be measured according to ASTM D 1308-02 (2013). For example, a water droplet can be deposited onto the cured curable composition and/or cured secondary composition and the water droplet can be covered with a glass container for a predefined period of time as mentioned above and at room temperature. The cured curable composition and/or cured secondary composition can then be monitored for blistering, discoloration, gloss loss, swelling, whitening, softening, and/or adhesion failure.

The cured curable composition and/or cured secondary composition can have a percent elongation of less than 10%, such as, for examples, less than 5%, less than 2%, less than 1%, or less than 0.1%. For example, the cured curable composition and/or cured secondary composition can have a percent elongation of 0. The percent elongation can be measured according to ASTM D 522/D522M-17. For example, the cured curable composition and/or cured secondary composition can be deposited on aluminum panels and subjected to bending using conical mandrel bend testing.

The curable composition and/or secondary composition according to the present disclosure can comprise Formula III and/or isomers thereof.

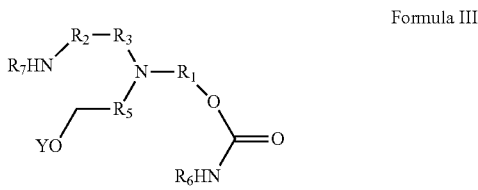

Formula III

Y can be at least one of a hydrogen atom, an alkyl group, an aryl group, and a carbamate group. Y can comprise a carbamate group and at least one of an alkyl group and an aryl group. Y can be a hydrogen atom. $R_6$ and Y can comprise an alkyl group or an aryl group that differ from one another. $R_6$ and Y can comprise the same alkyl group or aryl group.

The non-limiting and non-exhaustive example that follows is intended to further describe various non-limiting and non-exhaustive embodiments without restricting the scope of the embodiments described in this disclosure. Although the present disclosure describes a coating in the Example, those skilled in the art will appreciate it can also be equally applicable to an adhesive, a casting, a sealant, an elastomer, and a foam.

All quantities given in "parts" and "percent" are understood to be by weight, unless otherwise indicated.

EXAMPLE

N-2-hydroxyethylmorpholine-2, 3-dione (morpholinedione) was made in Covestro Labs. More specifically, in a 250 mL round bottom flask, 96 mL of diethyloxalate was added to 150 mL of isopropanol and was mixed. In an addition funnel, 75.0 parts diethanolamine was dissolved in 60 mL isopropanol and was mixed. The diethanolamine mixture was added to the diethyloxalate mixture drop-wise at room temperature and mixed for 12 hours to form morpholinedione. The formed morpholinedione was filtered out, washed with isopropanol, and dried in a vacuum oven.

The morpholinedione was reacted with DESMODUR N-3600 available from Covestro AG (Leverkusen, Germany) to obtain resin composition A. The synthesis was performed at 50° C. for several hours using T-12 catalyst (e.g., dibutylin dilaurate). Dimethylformamide (DMF) and acetone were added to reduce viscosity. The resin composition A has a morpholinedione equivalent weight of 542 in 63% by weight of DMF and acetone based on the total weight of the resin composition A.

Resin composition B was pure DESMODUR N-3600 available from Covestro AG (Leverkusen, Germany). Alcohol A was DIANOL 350 with hydroxyl equivalent weight of 280 available from Arkema (Colombes, France). Catalyst A was ADDOCAT 201 (dibutyltin dilaurate) catalyst available from Lanxess (Cologne, Germany).

The amines A-D as shown in Table I were used to prepare curable compositions A-H as shown in Table II.

TABLE I

| Amine A | 2-Methylpentamethylenediamine, commercially available from Invista as DYTEK A |
| Amine B | Isophorone diamine (IPDA) |
| Amine C | 4,4'-Diaminodicyclohexylmethane (PACM) |
| Amine D | 3,3'-dimethyl-4,4'-Diaminodicyclohexylmethane, commercially available from BASF as LAROMIN C260 |

Each curable composition A-H was prepared by adding acetone to resin composition A. The mixture was contacted with and reacted with an amine using a FLACKTEK speed mixer for one minute followed by application onto a panel using a drawdown bar. The panel was an iron phosphate treated ACT B1000, 4"×12" (10.2 cm×30.5 cm) test panel. Curable composition G was additionally applied to an aluminum chromate treated panel 4"×12" (10.2 cm×30.5 cm) test panel and an untreated aluminum 4"×12" (10.2 cm×30.5 cm) test panel for cross-hatch adhesion testing only. The dry film thickness of the curable compositions A-H was 15 µm on the panels. The curable compositions A-H were cured on the panels at various conditions such as, room temperature (e.g., 25° C.) for 16 hours, 80° C. for 16 hours, and 140° C. for three hours as shown in Table II.

Comparative curable composition I was prepared by mixing resin composition B with Alcohol A and Catalyst A. The mixture was applied onto panels using a drawdown bar. The panels used were an iron phosphate treated ACT B1000, 4"×12" (10.2 cm×30.5 cm) test panel and an untreated aluminum 4"×12" (10.2 cm×30.5 cm) test panel was used for cross-hatch adhesion testing only. The dry film thickness of the comparative curable composition I was 15 µm on the panels. The comparative curable composition I was cured on the panels at 140° C. for three hours as indicated in Table II.

The resulting panels were used to test the performance characteristics of the curable compositions A-H and comparative curable composition I, such as, microhardness, methyl ethyl ketone (MEK) double rubs, impact strength, elongation, water spot resistance, and cross-hatch adhesion.

Microhardness (e.g., Marten's hardness) measurements were done using FISCHERSCOPE HM2000 instrument according to DIN EN ISO 14577-1:2015. Microhardness readings were taken under a 20 mN test load run to a maximum of 5 µm indentation depths over a 20-second application time. Results shown in Table II are an average of three readings for each curable composition A-H and comparative curable composition I.

MEK double rubs were measured according to ASTM D4752-10(2015). Direct and reverse impact strength was measured according to ASTM D 2794-93(2019). Cross-hatch adhesion was measured according to ASTM D 3359-17. Elongation was measured according to ASTM D 522522M-17. Water spot resistance was measured according to ASTM D 1308-02(2013). Table II summarizes curable compositions A-H and comparative curable composition I.

TABLE 11

|  | A | B | C | D | E | F | G | H | I |
|---|---|---|---|---|---|---|---|---|---|
| Resin composition A (parts) | 9.30 | 9.30 | 4.50 | 4.50 | 4.18 | 4.18 | 4.18 | 4.33 | — |
| Resin composition B (parts) | — | — | — | — | — | — | — | — | 60.3 |
| Acetone (parts) | 10.0 | 10.00 | 5.00 | 5.00 | 5.00 | 5.00 | 5.00 | 5.00 | — |
| Amine A (parts) | 0.70 | 0.70 | — | — | — | — | — | — | — |
| Amine B (parts) | — | — | 0.50 | 0.50 | — | — | — | — | — |
| Amine C (parts) | — | — | — | — | 0.82 | 0.82 | 0.82 | — | — |
| Amine D (parts) | — | — | — | — | — | — | — | 0.67 | — |
| Alcohol A | — | — | — | — | — | — | — | — | 39.4 |
| Catalyst A | — | — | — | — | — | — | — | — | 0.3 |
| Curing temperature (° C.) | 25 | 80 | 25 | 80 | 25 | 80 | 140 | 80 | 140 |
| Curing time (h) | 16 | 16 | 16 | 16 | 16 | 16 | 3 | 16 | 3 |
| Microhardness (N/mm$^2$) | 2 | 4 | 2 | 8 | 2 | 25 | 149 | 0.5 | 60 |
| MEK double rubs | >100 | >100 | 180 | >300 | >200 | >200 | >200 | >200 | 40 |
| Impact strength (in-lbs) | — | — | — | — | — | — | >80D | — | >80D |
|  | — | — | — | — | — | — | >80R | — | >80R |

TABLE 11-continued

| | A | B | C | D | E | F | G | H | I |
|---|---|---|---|---|---|---|---|---|---|
| Elongation (%) | — | — | — | — | — | — | 0 | — | 0 |
| Water spot resistance (hrs) | — | — | — | — | <0.1 | <0.1 | >24 | — | >24 |
| Cross-hatch adhesion Steel Fe$_3$(PO$_4$)$_2$ treated | — | — | — | — | — | — | 5B | — | 5B |
| Cross-hatch adhesion Aluminum chromate treated | — | — | — | — | — | — | 5B | — | — |
| Cross-hatch adhesion Aluminum untreated | — | — | — | — | — | — | 5B | — | 5B |

As shown in Table II, curable compositions A-H have at least 100 MEK Double Rubs and curable compositions A-G have both 100 MEK Double Rubs and a microhardness of at least 2 N/mm$^2$. It was observed that microhardness values increased when the curing temperature was increased due to the evolution of DMF as solvent. For example, curing at 80° C. instead of 25° C. resulted in an improvement in the microhardness of 100% for curable compositions A-B, an improvement in the microhardness of 400% for curable compositions C-D, and an improvement in the microhardness of 1250% for compositions E-F. Curing at 140° C. instead of 80° C. resulted in a further improvement in the microhardness of 596% for curable compositions F-G.

As shown in Table II, the curable compositions A-H are morpholinedione based and cured with amines A-D and comparative curable composition I is polyisocyanate and polyol based (Alcohol A). Curable compositions A-H have minimal, if any, free isocyanate groups whereas comparative curable composition I has a plurality of free isocyanate groups. The curable compositions A-H have similar or in some examples better performance than comparative curable composition I. For example, curable compositions A-H have an improved MEK double rub performance compared to comparative curable composition I and curable composition G has an improved microhardness compared to comparative curable composition I.

It is believed that an adhesive, a casting, a sealant, an elastomer, and a foam would have similar performance characteristics to the coatings provided in the example. Additionally, other curable compositions formulated according to the present disclosure additionally can have improved performance characteristics.

Various aspects according to the present disclosure include, but are not limited to, the aspects listed in the following numbered clauses.

Clause 1. A method comprising: contacting a morpholinedione with an isocyanate to form a resin composition; and reacting the resin composition with an amine to form a curable composition.

Clause 2. The method according to Clause 1, wherein the reacting step comprises cross-linking the resin composition with the amine.

Clause 3. The method of according to Clause 2, wherein cross-linking further comprises a ring opening reaction.

Clause 4. The method according to any one of Clauses 1 to 3, further comprising curing the curable composition to form an article.

Clause 5. The method according to Clause 4, wherein the article is at least one component of at least one of an adhesive, a coating, a casting, a sealant, an elastomer, and a foam.

Clause 6. The method according to any one of Clauses 1 to 5, wherein the amine comprises a primary amine.

Clause 7. The method according to any one of Clauses 1 to 6, wherein the amine comprises at least one of diethylenetriamine, 2-methylpentamethylenediamine, isophrone diamine, 4,4'-diaminodicyclohexylmethane, 3, 3'-dimethyl-4, 4'diaminodicyclohexylmethane, ethylene diamine, ethylene triamine, propylene diamine, tetramethylene diamine, 1,6-hexamethylene diamine, bis(6-aminohexyl)ether, tricyclodecane diamine, N,N'-dimethyldiethyltriamine, cyclohexyl-1,2,4-triamine, cyclohexyl-1,2,4,5-tetraamine, 3,4,5-triaminopyran, 3,4-diaminofuran, cycloaliphatic diamines, triaminononane, polyether amine, and a polyaspartic ester based amine.

Clause 8. The method according to any one of Clauses 1 to 7, wherein the morpholinedione comprises a N-hydroxyethylmorpholine-2, 3-dione.

Clause 9. The method according to any one of Clauses 1 to 8, wherein the isocyanate has a functionality of at least 2.

Clause 10. The method according to any one of Clauses 1 to 9, wherein the isocyanate is selected from the group consisting of 1,4-tetramethylene diisocyanate, 1,6-hexamethylene diisocyanate, 2,2,4- and 2,4,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate—bio-based), -methylpentamethylene 1,5-diisocyanate, lysine and lysine ester diisocyanate, 1,4-diisocyanato-2,2,6-trimethylcyclohexane (TMCDI), 1,3- and 1,4-bis(isocyanatomethyl)cyclohexane), m- and p-tetramethyl-1,3-xylylene diisocyanate, m- and p-tetramethyl-1,4-xylylene diisocyanate, bis(1-isocyanato-1-methylethyl) naphthalene, 1,3- and 1,4-phenylene diisocyanate, 2,3,5,6-tetramethyl-1,4-diisocyanatobenzene, naphthalene 1,5-diisocyanate (NID), 3,3'-dimethyl-4,4'-diisocyanatobiphenyl (TOBI); oligomers, polymers, isomers thereof, and combinations thereof.

Clause 11. The method according to any one of Clauses 1 to 10, wherein the isocyanate comprises at least one of a polyurethane resin, a polyurea resin, an acrylic resin, a polyester resin, a polycarbonate resin, a polysiloxane resin, an epoxy resin, a melamine resin, and a phenol formaldehyde resin.

Clause 12. The method according to any one of Clauses 1 to 11, wherein the curable composition has a free hydroxyl group.

Clause 13. The method according to any one of Clauses 1 to 12, further comprising contacting the curable composition with a second isocyanate to form a secondary curable composition, wherein the second isocyanate is different than or the same as the first isocyanate.

Clause 14. An article produced by the process, comprising: contacting a morpholinedione with an isocyanate to form a resin composition; and reacting the resin composition with an amine to form a curable composition.

Clause 15. The article according to Clause 14, wherein the morpholinedione comprises a N-hydroxyethylmorpholine-2, 3-dione.

Clause 16. The article according one of Clauses 14 and 15, wherein the curable composition has a free hydroxyl group.

Clause 17. The article according to any one of Clauses 14 to 16, further comprising contacting the curable composition with a second isocyanate to form a secondary curable composition.

Clause 18. The article according to Clause 17, wherein the second isocyanate is different than the first isocyanate.

Clause 19. The article according to Clause 17, wherein the second isocyanate is the same as the first isocyanate.

Clause 20. The article according to any one of Clauses 14 to 19, wherein the curable composition has a microhardness of at least 2 N/mm² according to DIN EN ISO 14577-1: 2015.

Clause 21. The article according to any one of Clauses 14 to 20, wherein the curable composition has a methyl ethyl ketone rub resistance of at least 100 double rubs according to ASTM D4752-10(2015).

Clause 22. The article according to any one of Clauses 14 to 21, wherein the curable composition has a cross-hatch adhesion of at least 4B according to ASTM D 3359-17.

Clause 23. The article according to any one of Clauses 14 to 22, wherein the article is at least one component of at least one of a coating, an adhesive, a casting, a sealant, an elastomer, and a foam.

Clause 24. A curable composition comprising the following structure:

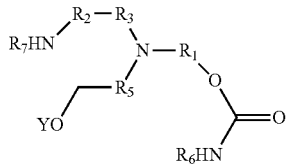

wherein $R_1$ is an alkyl bridging group, two of $R_2$, $R_3$, and $R_5$ are a carbonyl group and the remaining one of $R_2$, $R_3$, and $R_5$ is a methylene bridge, $R_6$ is an alkyl group or an aryl group, $R_7$ is an alkyl group or an aryl group, and Y is at least one of a hydrogen atom, an alkyl group, an aryl group, and a carbamate group.

Clause 25. The curable composition according to Clause 24, wherein Y comprises a carbamate group and one of an alkyl group and an aryl group.

Clause 26. The curable composition according to Clause 25, wherein $R_6$ comprises a different alkyl group or aryl group than Y.

Clause 27. The curable composition according to Clause 24, wherein Y is a hydrogen atom.

Clause 28. The curable composition according to any one of Clauses 24 to 27, wherein the composition is at least one component of at least one of a coating, an adhesive, a casting, a sealant, an elastomer, and a foam.

Clause 29. A product that is formed by the curable composition according to any one of Clauses 24 to 28.

Various features and characteristics are described in this specification to provide an understanding of the composition, structure, production, function, and/or operation of the invention, which includes the disclosed compositions, coatings, and methods. It is understood that the various features and characteristics of the invention described in this specification can be combined in any suitable manner, regardless of whether such features and characteristics are expressly described in combination in this specification. The Inventors and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements.

What is claimed is:

1. A method comprising:
   contacting a morpholinedione with an isocyanate to form a resin composition; and
   reacting the resin composition with an amine to form a curable composition.

2. The method according to claim 1, wherein the reacting step comprises cross-linking the resin composition with the amine.

3. The method according to claim 2, wherein cross-linking further comprises a ring opening reaction.

4. The method according to claim 1, further comprising curing the curable composition to form an article.

5. The method according to claim 4, wherein the article is at least one component of at least one of an adhesive, a coating, a casting, a sealant, an elastomer, and a foam.

6. The method according to claim 1, wherein the amine comprises a primary amine.

7. The method according to claim 1, wherein the amine comprises at least one of diethylenetriamine, 2-methylpentamethylenediamine, isophrone diamine, 4,4'-diaminodicyclohexylmethane, 3, 3'-dimethyl-4, 4'diaminodicyclohexylmethane, ethylene diamine, ethylene triamine, propylene diamine, tetramethylene diamine, 1,6-hexamethylene diamine, bis(6-aminohexyl)ether, tricyclodecane diamine, N,N'-dimethyldiethyltriamine, cyclohexyl-1,2,4-triamine, cyclohexyl-1,2,4,5-tetraamine, 3,4,5-triaminopyran, 3,4-diaminofuran, cycloaliphatic diamines, triaminononane, polyether amine, and a polyaspartic ester based amine.

8. The method according to claim 1, wherein the morpholinedione comprises a N-hydroxyethylmorphonline-2, 3-dione.

9. The method according to claim 1, wherein the isocyanate has a functionality of at least 2.

10. The method according to claim 1, wherein the isocyanate is selected from the group consisting of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate—bio-based), 2-methyl-pentamethylene 1,5-diisocyanate, lysine and lysine ester diisocyanate, 1,4-diisocyanato-2,2,6-trimethylcyclohexane (TMCDI), 1,3- and 1,4-bis(isocyanatomethyl)cyclohexane), m- and p-tetramethyl-1,3-xylylene diisocyanate, m- and p-tetramethyl-1,4-xylylene diisocyanate, bis(1-isocyanato-1-methylethyl)naphthalene, 1,3- and 1,4-phenylene diisocyanate, 2,3,5,6-tetramethyl-1,4-diisocyanatobenzene, naphthalene 1,5-diisocyanate (NID), 3,3'-dimethyl-4,4'-diisocyanatobiphenyl (TOBI); oligomers, polymers, isomers thereof, and combinations thereof.

11. The method according to claim 1, wherein the isocyanate comprises at least one of a polyurethane resin, a polyurea resin, an acrylic resin, a polyester resin, a polycarbonate resin, a polysiloxane resin, an epoxy resin, a melamine resin, and a phenol formaldehyde resin.

12. The method according to claim 1, wherein the curable composition has a free hydroxyl group.

13. The method according to claim 1, further comprising contacting the curable composition with a second isocyanate to form a secondary curable composition, wherein the second isocyanate is different than or the same as the first isocyanate.

14. An article produced by the process, comprising:
contacting a morpholinedione with an isocyanate to form a resin composition; and
reacting the resin composition with an amine to form a curable composition.

15. The article according to claim 14, wherein the morpholinedione comprises a N-hydroxyethylmorpholine-2,3-dione.

16. The article according to claim 14, wherein the curable composition has a free hydroxyl group.

17. The article according to claim 14, further comprising contacting the curable composition with a second isocyanate to form a secondary curable composition.

18. The article according to claim 17, wherein the second isocyanate is different than the first isocyanate.

19. The article according to claim 17, wherein the second isocyanate is the same as the first isocyanate.

20. The article according to claim 14, wherein the curable composition has a microhardness of at least 2 N/mm$^2$ according to DIN EN ISO 14577-1:2015.

21. The article according to claim 14, wherein the curable composition has a methyl ethyl ketone rub resistance of at least 100 double rubs according to ASTM D4752-10(2015).

22. The article according to claim 14, wherein the curable composition has a cross-hatch adhesion of at least 4B according to ASTM D 3359-17.

23. The article according to claim 14, wherein the article is at least one component of at least one of a coating, an adhesive, a casting, a sealant, an elastomer, and a foam.

24. A curable composition comprising the following structure:

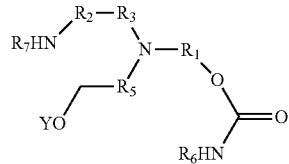

wherein
$R_1$ is an alkyl bridging group,
two of $R_2$, $R_3$, and $R_5$ are a carbonyl group and the remaining one of $R_2$, $R_3$, and $R_5$ is a methylene bridge,
$R_6$ is an alkyl group or an aryl group,
$R_7$ is an alkyl group or an aryl group, and
Y is at least one of a hydrogen atom, an alkyl group, an aryl group, and a carbamate group.

25. The curable composition according to claim 24, wherein Y comprises a carbamate group and one of an alkyl group and an aryl group.

26. The curable composition according to claim 25, wherein $R_6$ comprises a different alkyl group or aryl group than Y.

27. The curable composition according to claim 24, wherein Y is a hydrogen atom.

28. The curable composition of claim 24, wherein the composition is at least one component of at least one of a coating, an adhesive, a casting, a sealant, an elastomer, and a foam.

29. A product that is formed by the curable composition according to claim 24.

* * * * *